(12) United States Patent
Kim et al.

(10) Patent No.: US 9,988,618 B2
(45) Date of Patent: Jun. 5, 2018

(54) PSICOSE EPIMERASE AND PSICOSE PRODUCTION METHOD USING SAME

(71) Applicant: DAESANG CORPORATION, Seoul (KR)

(72) Inventors: Tae Gyun Kim, Seoul (KR); Min Su Kim, Seoul (KR); Tae Yong Kim, Seoul (KR); Eun Bum Song, Seoul (KR); Deok Kun Oh, Gyeonggi-do (KR)

(73) Assignee: DAESANG CORPORATION, Seoul (KR)

( * ) Notice: Subject to any disclaimer, the term of this patent is extended or adjusted under 35 U.S.C. 154(b) by 0 days. days.

(21) Appl. No.: 15/128,812

(22) PCT Filed: May 22, 2015

(86) PCT No.: PCT/KR2015/005208
§ 371 (c)(1),
(2) Date: Sep. 23, 2016

(87) PCT Pub. No.: WO2015/182937
PCT Pub. Date: Dec. 3, 2015

(65) Prior Publication Data
US 2017/0101637 A1    Apr. 13, 2017

(30) Foreign Application Priority Data
May 28, 2014    (KR) .......................... 10-2014-0064651

(51) Int. Cl.
*C12P 19/24*    (2006.01)
*C12N 9/90*    (2006.01)
*C12N 11/00*    (2006.01)
*C12P 19/02*    (2006.01)

(52) U.S. Cl.
CPC ................ *C12N 9/90* (2013.01); *C12P 19/02* (2013.01); *C12P 19/24* (2013.01); *C12Y 501/03* (2013.01)

(58) Field of Classification Search
None
See application file for complete search history.

(56) References Cited

U.S. PATENT DOCUMENTS

| | | | | |
|---|---|---|---|---|
| 8,030,035 B2 * | 10/2011 | Oh | ........................ | C12N 9/90 435/94 |
| 9,217,166 B2 * | 12/2015 | Kim | ...................... | C12P 19/02 |
| 2012/0244580 A1 | 9/2012 | Hung et al. | ................... | 435/105 |
| 2014/0199732 A1 * | 7/2014 | Kim | ...................... | C12P 19/02 435/94 |

FOREIGN PATENT DOCUMENTS

| | | | | |
|---|---|---|---|---|
| KR | 10-0744479 | 7/2007 | ............... | C12N 9/90 |
| KR | 10-0832339 | 5/2008 | ............... | C12N 1/20 |
| KR | 10-2011-0035805 | 4/2011 | ............... | C12P 19/20 |
| KR | 10-1106253 | 1/2012 | ............... | C12N 1/21 |
| KR | 10-1203856 | 11/2012 | ............... | C12N 9/92 |
| KR | 10-1318422 | 10/2013 | ............... | C12N 9/90 |
| KR | 10-1339443 | 11/2013 | ............... | C12N 9/90 |
| KR | 10-2014-0021974 | 2/2014 | ............... | C12N 9/90 |
| WO | WO 2006/129554 A1 | 12/2006 | ............ | H04N 1/387 |
| WO | WO 2011/040708 A2 | 4/2011 | ............. | C12P 19/20 |
| WO | WO 2014/049373 A1 | 4/2014 | ............. | C12P 19/02 |

OTHER PUBLICATIONS

Branden et al. Introduction to Protein Structure, Garland Publishing Inc., New York, p. 247, 1991.*
Extended European Search Report, dated Aug. 18, 2017, issued in European Patent Application No. 15800046.3.
Japanese Office Action dated Jul. 18, 2017, issued in Japanese Patent Application No. 2017-503758.
AP endonuclease, family 2 [Flavonifractor plautii ATCC 29863], GenBank/GenPept accession No. EHM40452, (Dec. 21, 2011), [retrieved on Jul. 7, 2017], Retrieved from the Internet, URL, https://www.ncbi.nih.gov/protein/EHM40452._1?report=girevhist.
AP endonuclease, family 2 [Clostridium sp. ATCC BAA-442], GenBank/GenPept accession No. ERI77062, (Sep. 12, 2013), [retrieved on Jul. 7, 2017], Retrieved from the Internet, URL, https://www.ncbi.nlm.nih.gov/protein/ERI77062._1?report=girevhist.
Mu, W. et al., (2011) "Cloning, expression, and characterization of a D-psicose 3-epimerase from *Clostridium cellulolyticum* H10.", *J. Agric. Food Chem.*, vol. 59, pp. 7785-7792.

(Continued)

*Primary Examiner* — Yong D Pak
(74) *Attorney, Agent, or Firm* — Harness, Dickey & Pierce, P.L.C.

(57) ABSTRACT

The present invention provides a novel psicose epimerase derived from *Flavonifractor plautii* and capable of converting fructose to psicose. The novel psicose epimerase according to the present invention possesses an activity producing psicose by epimerizing the carbon-3 position of fructose, and has maximal activity for the conversion of fructose to psicose at a relatively high temperature and a pH less than or equal to neutral, has excellent thermal stability, and can mass-produce psicose from fructose in a high yield for a short amount of time. Therefore, the psicose epimerase according to the present invention is advantageous in the industrial production of psicose, and it is expected that the psicose produced thereby can be usefully utilized in the functional sugar industry and also as materials for health food, medicine, cosmetics, and the like using the psicose.

6 Claims, 7 Drawing Sheets

(56) References Cited

OTHER PUBLICATIONS

Mu W. et al., (2012) "Recent advances on applications and biotechnological production of D-psicose.", *Applied Microbiology and Biotechnology*, Springer, Berlin, DE, May 10, 2012, vol. 94, No. 6, pp. 1461-1467, XP035060669.
Mu, W., et al., (2013) "Characterization of a D-psicose producing enzyme, D-psicose 3-epimerase, from *Clostridium* sp.", *Biotechnol. Lett.*, vol. 35, pp. 1481-1486.
NCBI GenBank Accession Reference Sequence No. WP_007494289, "Multispecies: AP endonuclease [Clostridiales].", May 9, 2013.
International Search Report (ISR) dated Jun. 26, 2015 in PCT/KR2015/005208, with English translation.

\* cited by examiner

PSICOSE EPIMERASE AND PSICOSE PRODUCTION METHOD USING SAME

CROSS-REFERENCE TO RELATED APPLICATIONS

This application is a national phase application of PCT Application No. PCT/KR2015/005208, filed on May 22, 2015, which claims the benefit and priority to Korean Patent Application No. 10-2014-0064651, filed May 28, 2014. The entire disclosures of the applications identified in this paragraph are incorporated herein by references.

FIELD

The present invention relates to a novel psicose epimerase capable of converting fructose into D-psicose, a method of producing the psicose epimerase from a recombinant strain, a method of producing D-psicose from fructose using the same, and the like.

BACKGROUND

D-psicose as an epimer of a carbon-3 position of fructose has 70% sweetness as compared with sugar (Oshima 2006), but is functional monosaccharide applicable as a low-calorie sweetener of diet food in which energy is only 0.3% (Matsuo et al. 2002). Further, the D-psicose serves to inhibit glucose by suppressing absorption of glucose to be applied to food for diabetic patients, receiving food, and the like and serves to suppress the enzyme activity associated with lipid synthesis in the liver to suppress the accumulation of abdominal fat to be used in various functional foods such as health foods (Matsuo et al. 2001; Iida et al. 2008; Hayashi et al. 2010; Hossain et al. 2011).

As the above features, the psicose is a good source capable of replacing sugar, but the psicose belongs to a rare saccharide as a monosaccharide that is rarely present in the nature, and thus, a method for efficiently producing the psicose is required so as to be applied to food industry. The psicose is mostly produced through a chemical process as an existing method of producing the psicose. Bilik, et al. propose a method of converting fructose into psicose by using a catalytic action of molybdate ions. McDonald produced the psicose by a 3-step chemical treatment process from 1,2:4,5-di-δ-isopropylidene-beta-D-fructopyranose. Further, Doner produced the psicose by heating the fructose together with ethanol and trimethylamine. However, there are disadvantages in that a lot of costs are consumed in the chemical production methods, whereas the efficiencies thereof are low and a lot of byproducts are generated.

As a biological production method of psicose, a method of producing psicose from galactitol, D-tagatose, D-talitol, or the like by using a cell reaction of a microorganism is proposed (Ken Izumori). However, the method is difficult to be applied to the industrial production because the substrate is the rare saccharide. The most efficient method for industrialization is a method of finding an enzyme for converting fructose into psicose in a D-ketose 3-epimerase group. By the existing reported contents, the psicose was produced from the fructose by using a D-tagatose 3-epimerase which is expressed in *E. coli* transformed by inserting and transforming the D-tagatose 3-epimerase derived from *Clostridium celluloticum* H (10) (Mu et al. 2011), *Agrobacterium tumefaciens* (Kim et al. 2006), *Pseudomonas cichorii* (Itoh et al. 1994), *Rhizobium spheroides* (Zhang et al. 2009) in *E. coli*. With relation to a technique of producing psicose from fructose by using an enzyme, in Korea Patent Registration No. 10-0744479, a method of producing psicose by a psicose epimerase derived from *Agrobacterium tumefaciens* is disclosed, in Korea Patent Registration No. 10-0832339, *Sinorhizobium* YB-58 KCTC 10983BP having an activity of converting fructose into psicose and a method for converting fructose into psicose by using the same are disclosed, in Korea Patent Registration No. 10-1106253, *E. coli* including a polynucleotide coding a psicose 3-epimerase of *Agrobacterium tumefaciens* C58 having an activity of catalyzing conversion of fructose into psicose and a method of producing psicose from fructose by using the same are disclosed, in Korea Patent Registration No. 10-1339443 (Korea Patent Application Publication No. 10-2008-0071176), a ketose 3-epimerase derived from microorganisms belonging to genus *Rhizobium* and a method for converting fructose into psicose by using the same are disclosed, and in Korea Patent Registration No. 10-1318422, a D-psicose 3-epimerase derived from *Clostridiuim scindens* and a method for producing psicose from fructose by using the same are disclosed.

However, according to an existing enzymatic method of which functions are known, a method of producing psicose is best at a medium temperature and pH of an alkaline condition. In the alkaline condition, the reaction induces non-specific reaction and browning of sugar, and thus is not suitable for the industrialization. Further, there is a problem in that the existing enzymes have factors of increasing producing costs for producing psicose which is applied to the industrialization due to deteriorated stability or a slow reaction rate at a high temperature. Therefore, development of a novel D-psicose 3-epimerase in which a product yield, a temperature, a pH and a reaction rate of the psicose are suitable for industrialization is required. With relation to this, in Korea Patent Application Publication No. 10-2014-0021974, a D-psicose 3-epimerase derived from *Treponema primitia* ZAS-1 having a rapid psicose conversion rate and stability at a high temperature by inducing mutation at a gene level is disclosed, and in Korea Patent Registration No. 10-1203856, psicose epimerase variants having improved thermal stability obtained by mutation of a wild-type psicose epimerase derived from *Agrobacterium tumefaciens* is disclosed.

DISCLOSURE OF INVENTION

Technical Problem

A first object of the present invention is to provide a novel D-psicose 3-epimerase having an activity of converting fructose into psicose, a maximum activity at a relatively high temperature or a pH less than or equal to neutral, and excellent thermal stability.

A second object of the present invention is to provide a method of producing a novel D-psicose 3-epimerase or various elements required for producing the novel D-psicose 3-epimerase.

A third object of the present invention is to provide a method of producing psicose from fructose or various elements required for producing the psicose from the fructose.

Solution to Problem

The inventors of the present invention discovered that an enzyme derived from *Flavonifractor plautii* has a high activity for converting fructose into psicose, excellent thermal stability, and an optimal activity in a high temperature range and a pH range corresponding to neutral or weak acid, and thus, completed the present invention.

In order to solve the first object, an aspect of the present invention provides a psicose epimerase consisting of an amino acid sequence of SEQ ID NO: 1.

In order to solve the second object, another aspect of the present invention provides a polynucleotide coding a psicose epimerase consisting of an amino acid sequence of SEQ ID NO: 1. Further, the present invention provides a primer pair for synthesizing the polynucleotide coding the psicose epimerase consisting of the amino acid sequence of SEQ ID NO: 1. Further, the present invention provides a recombinant vector including the polynucleotide coding the psicose epimerase consisting of the amino acid sequence of SEQ ID NO: 1. Further, the present invention provides a recombinant strain which is transformed by the polynucleotide coding the psicose epimerase consisting of the amino acid sequence of SEQ ID NO: 1 or the recombinant vector including the polynucleotide coding the psicose epimerase consisting of the amino acid sequence of SEQ ID NO: 1. Further, the present invention provides a method for producing psicose epimerase, in which the method includes steps of: expressing the psicose epimerase by culturing a recombinant strain which is transformed by a polynucleotide coding the psicose epimerase consisting of the amino acid sequence of SEQ ID NO: 1 or a recombinant vector including the polynucleotide coding the psicose epimerase consisting of the amino acid sequence of SEQ ID NO: 1; and isolating the psicose epimerase from a lysate of the recombinant strain with the expressed psicose epimerase.

In order to solve the third object, yet another aspect of the present invention provides a composition for producing psicose including a psicose epimerase consisting of an amino acid sequence of SEQ ID NO: 1. Further, the present invention provides the composition for producing psicose including a recombinant strain which is transformed by a polynucleotide coding the psicose epimerase consisting of the amino acid sequence of SEQ ID NO: 1 or a recombinant vector including the polynucleotide coding the psicose epimerase consisting of the amino acid sequence of SEQ ID NO: 1, a culture of the recombinant strain, or a lysate of the recombinant strain. Further, the present invention provides the method for producing psicose, in which the method includes reacting fructose with the psicose epimerase consisting of an amino acid sequence of SEQ ID NO: 1 or the composition including the psicose epimerase. Further, the present invention provides the method for producing psicose, in which the method includes reacting fructose with the recombinant strain which is transformed by the polynucleotide coding the psicose epimerase consisting of the amino acid sequence of SEQ ID NO: 1 or the recombinant vector including the polynucleotide coding the psicose epimerase consisting of the amino acid sequence of SEQ ID NO: 1, a culture of the recombinant strain, a lysate of the recombinant strain, or the composition including one or more thereof.

Advantageous Effects

The novel psicose epimerase, according to the present invention, possesses an activity producing psicose by epimerizing the carbon-3 position of fructose, and has maximal activity for the conversion of fructose into psicose at a relatively high temperature and a pH less than or equal to neutral, has excellent thermal stability, and can mass-produce psicose from fructose in a high yield for a short amount of time. Therefore, the psicose epimerase according to the present invention is advantageous in the industrial production of psicose, and the psicose produced thereby can be usefully utilized in the functional sugar industry and as materials for health food, medicine, cosmetics, and the like using the psicose.

BRIEF DESCRIPTION OF DRAWINGS

In FIG. 3, an enzyme activity in the case of treating each metal ion is relatively represented by setting an enzyme activity in a control group to 100.

In FIG. 5, the enzyme activity is relatively represented by setting a maximum activity to 100.

In FIG. 6, the enzyme activity is relatively represented by setting a maximum activity to 100.

In FIG. 7, the enzyme activity is relatively represented by setting an enzyme activity of a reaction using psicose as a substrate to 100.

DETAILED DESCRIPTION

Figure 1:
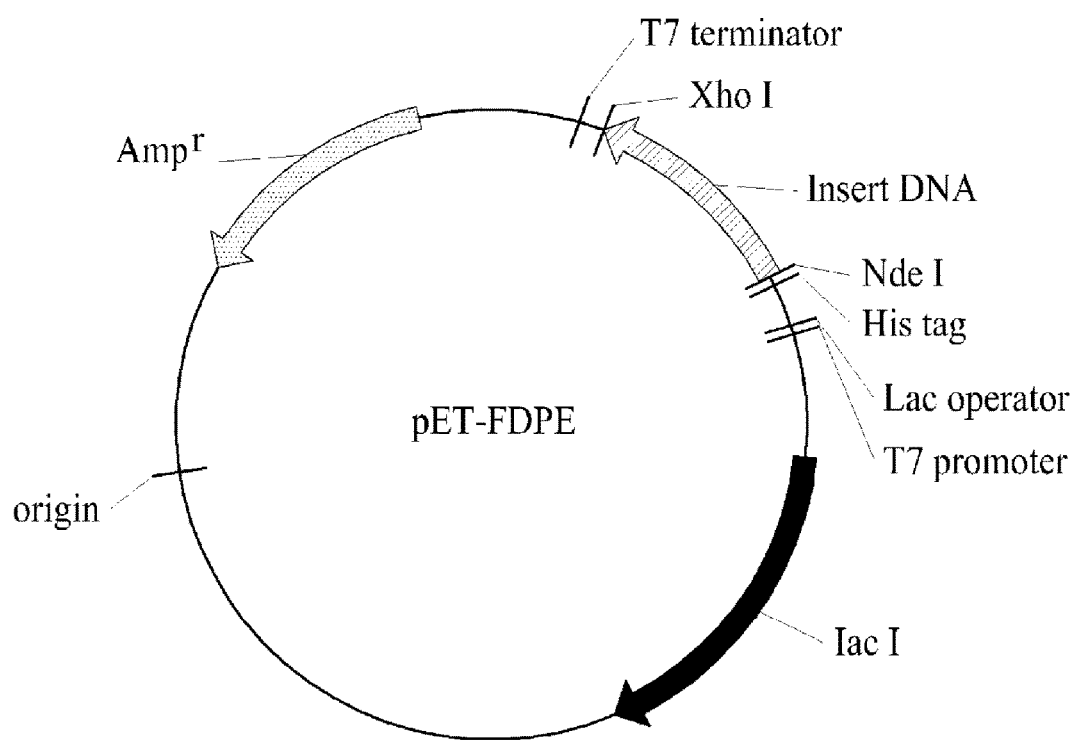
FIG. 1 is a cleavage map of pET-FDPE which is a recombinant expression vector.

Hereinafter, the present invention will be described in detail.

The present invention relates to a novel D-psicose 3-epimerase (hereinafter, referred to as a psicose epimerase) capable of converting fructose into psicose. The psicose epimerase is derived from *Flavonifractor plautii*, and has maximal activity for the conversion of the fructose into the psicose at a relatively high temperature and a pH less than or equal to neutral, has excellent thermal stability, and can mass-produce the psicose from the fructose in a high yield for a short amount of time. The psicose epimerase may be obtained by a method of amplifying a specific DNA in many DNAs present in a *Flavonifractor plautii* genomic DNA by a polymerase reaction, preparing a recombinant expression vector by inserting the amplified specific DNA to an expression vector, producing a recombinant strain by transforming a host strain with the recombinant expression vector, and then culturing and expressing the recombinant strain. The psicose epimerase according to the present invention preferably has a molecular weight of 30 to 34 kDa, an optimal activity temperature in a range of 55 to 67° C., and an optimal activity pH in a range of 6.5 to 8. The psicose epimerase according to the present invention consists of an amino acid sequence of SEQ ID NO: 1, but an equivalent range of the psicose epimerase according to the present invention is not limited thereto. For example, in the equivalent range of the psicose epimerase according to the present invention, so long as the activity of converting the fructose into the psicose is maintained, some of amino acids of SEQ ID NO: 1 may be replaced, inserted, and/or deleted. Preferably, the replacement of the amino acid may be performed by conservative amino acid replacement in which a characteristic of a protein is not changed. Further, the modification of the amino acid may be performed by glycosylation, acetylation, phosphorylation, and the like. Further, the equivalent range of the psicose epimerase according to the present invention may include a protein with increased structural stability to heat, pH, and the like by mutation or modification of the amino acid sequence or increased activity for the conversion of fructose into psicose. Further, the equivalent range of the psicose epimerase according to the present invention may include amino acid sequences having homology of 70% or more, 80% or more, 90% or more, 95% or more, or 99% or more with the amino acid sequence of SEQ ID NO: 1. The following Table 1 lists amino acids which may replace amino acids in the protein by the conservative amino acid replacement.

TABLE 1

| Amino acid residues in peptide | Conservative replacement group |
|---|---|
| Ala | Ser |
| Arg | Lys |
| Asn | Gln, His |
| Asp | Glu |
| Gln | Asn |
| Cys | Ser |
| Glu | Asp |
| Gly | Pro |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr, Gly |
| Thr | Ser, Val |
| Trp | Tyr |
| Tyr | Trp, Phe |
| Val | Ile, Leu |

Another exemplary embodiment of the present invention relates to a method of producing a novel psicose epimerase or various elements required for producing the novel psicose epimerase. The various elements required for producing the novel psicose epimerase include polynucleotide, a primer pair, a recombinant vector, a recombinant strain, and the like.

The polynucleotide is polynucleotide coding an epimerase consisting of an amino acid sequence of SEQ ID NO: 1 and preferably consists of a base sequence of SEQ ID NO: 2. In the present invention, the term "polynucleotide" means all of non-modified or modified polyribonucleotides (RNA) or polydeoxyribonucleotides (DNA). The polynucleotide includes single- or double-stranded DNA, DNA which is a mixture of single- and double-stranded regions, single- and double-stranded RNA, RNA which is a mixture of single- and double-stranded regions, or hybrid molecules thereof, but is not limited thereto. Further, the equivalent range of the polynucleotide coding the epimerase includes a sequence having the substantial identity with a base sequence of SEQ ID NO: 2. The substantial identity means that any other sequence is arranged to maximally correspond to the base sequence of SEQ ID NO: 2 and the any other sequence has the sequence homology of 70% or more, 90% or more, or 98% or more with the base sequence of SEQ ID NO: 2 by analyzing the sequence thereof. It can be easily understood to those skilled in the art that one or more bases of the base sequence of the polynucleotide are replaced, added, or deleted by using a gene recombination technique known in the art to produce polynucleotide coding an enzyme having the same activity in a range having the substantial homology. A comparison of the homologies may be performed by calculating homology between two or more sequences in percentage (%) by using a computer program on the market.

Further, the primer pair is to synthesize polynucleotide coding a psicose epimerase consisting of an amino acid sequence of SEQ ID NO: 1, and preferably constituted by a forward primer having a base sequence of SEQ ID NO: 3 and a reverse primer having a base sequence of SEQ ID NO: 4.

Further, the recombinant vector includes polynucleotide coding the psicose epimerase consisting of the amino acid sequence of SEQ ID NO: 1. The recombinant vector may be provided in a form of inserting the polynucleotide coding the psicose epimerase into a cloning vector or an expression vector by using a known standard method. In the present invention, the term "cloning vector" is defined as a material which can transport a DNA fragment into a host cell and reproduce the DNA fragment. In the present invention, the cloning vector may further include a polyadenylation signal, a transcription termination sequence, and a multiple cloning site. In this case, the multiple cloning sites include at least one endonuclease restriction site. Further, the cloning vector may further include a promoter. As an example, in the present invention, the polynucleotide coding the psicose epimerase may be located at the upstream of the polyadenylation signal and the transcription termination sequence, and at least one endonuclease restriction site may be located at the upstream of the polyadenylation signal and the transcription termination sequence. Further, in the present invention, the term "expression vector" is defined as a DNA sequence required for transcription and translation of the cloned DNA in an appropriate host. Further, in the present invention, the term "expression vector" means a gene construct including a required regulation element which is operably connected to an insertion so as to express the insertion in cells of an object. The expression vector may be produced and purified by using a standard recombinant DNA technique. A kind of expression vector is not particularly limited as long as the expression vector expresses a desired gene in various host cells, such as, prokaryotic and eukaryotic cells and performs a function of producing a desired protein, but is preferably a vector which may mass-produce a foreign protein in a similar form to a natural state, while possessing a promoter representing a strong activity and strong expression force. The expression vector preferably includes at least a promoter, an initiation codon, a gene coding a desired protein, and a stop codon terminator. In addition, the expression vector may appropriately include a DNA coding a signal peptide, an additional expression regulating sequence, non-translation regions of 5'-terminal and 3'-terminal of a desired gene, a selection marker region, a replicable unit, or the like. The "promoter" means a minimal sequence enough to indicate the transcription. Further, a promoter configuration enough to express a regulatory promoter-dependent gene induced by a cell type-specific or external signal or agent may be included, and the configurations may be located at the 5' or 3' portion of the gene. Both a conservative promoter and an induction promoter are included. The promoter sequence may be derived from prokaryote, eukaryote, or virus. The term "operably connected" means that one function is regulated by another thing by association with a polynucleotide sequence on a single polynucleotide. For example, in the case where the promoter may control expression of the coding sequence (that is, the coding sequence is under the transcription regulation of the promoter), if the promoter is connected with the coding sequence to operate or a ribosome binding site is located to promote the translation, the ribosome binding site is connected to the coding sequence and operates. The coding sequence may be connected to a regulation sequence and operate in a sense direction or an antisense direction. In the expression vector according to the present invention, the recombinant vector is preferably an expression vector and the expression vector preferably has a cleavage map of FIG. 1

Further, the recombinant strain is transformed by the polynucleotide coding the psicose epimerase consisting of the amino acid sequence of SEQ ID NO: 1 or transformed by a recombinant vector including the polynucleotide coding the psicose epimerase consisting of the amino acid sequence of SEQ ID NO: 1. In the present invention, the term "recombinant strain" means cells transformed by introducing a polynucleotide coding one or more target proteins or an expression vector having the polynucleotide to a host cell. A method for producing a transformant by introducing the expression vector to the host cell includes a chemical treating method including transient transfection, microinjection, transduction, cell fusion, calcium phosphate precipitation, liposemmediated transfection, DEAE Dextran-mediated transfection, polybrene-mediated transfection, electroporation, electroinjection, PEG, and the like, a method using a gene gun and the like, and the like, but is not limited thereto. In the present invention, as long as a host cell which may be transformed by the expression vector is known in the art, such as prokaryotic cells, plant cells, insect cells, animal cells, and the like, a kind thereof is largely not limited thereto. Preferably, a host having high introduction efficiency of DNA and high expression efficiency of the introduced DNA is generally used. For example, the host cell may be *E. coli*. The *E. coli* includes BL21, JM109, K-12, LE392, RR1, DH5α, W3110, or the like, but is not limited thereto. In addition, the host cell may be a strain selected from the group consisting of *Bacillus* strains such as *Bacillus subtilis* and *Bacillus thuringiensis*, Coryne bacterial strains such as *Corynebacterium glutamicum, Salmonella* strains such as *Salmonella typhimurium*, other *Serratia marcescens*, and Enterobacteriaceae strains such as various *Pseudomonas* species.

Further, a method of producing the psicose epimerase includes the steps of expressing psicose epimerase by culturing a recombinant strain which is transformed by a polynucleotide coding the psicose epimerase consisting of the amino acid sequence of SEQ ID NO: 1 or a recombinant vector including the polynucleotide coding the psicose epimerase consisting of the amino acid sequence of SEQ ID NO: 1; and isolating the psicose epimerase from a lysate of the recombinant strain in which the psicose epimerase is expressed. The expression of the protein by the host cell may be induced by using isopropyl-1-thio-β-D-galactopyranoside (IPTG) as an inducing factor and an inducing time may be adjusted to maximize the amount of the protein. In the present invention, the psicose epimerase may be collected from a lysate of the recombinant strain. The cells used in protein expression may be lysed by various physical or chemical means such as freeze-thawing repetition, sonication, mechanical breakage, or a cell lytic agent and can be isolated or purified by a general biochemical isolation technique (Sambrook et al., Molecular Cloning: A laboratory Manual, (2nd Ed., Cold Spring Harbor Laboratory Press, 1989; Deuscher, M., Guide to Protein Purification Methods Enzymology, Vol. 182. Academic Press. Inc., San Diego, Calif., 1990). For example, the method of isolating or purifying the protein expressed by the host cell includes electrophoresis, centrifugation, gel filtration, precipitation, dialysis, chromatography (ion exchange chromatography, affinity chromatography, immunosorbent affinity chromatography, reverse-phase HPLC, and gel permeation HPLC), isoelectricity focus, and various modified or complex methods thereof, but is not limited thereto. Meanwhile, in the present invention, the isolating of the psicose epimerase from the lysate of the recombinant strain may be preferably performed by affinity chromatography using a peptide tag. As the peptide tag, various known tags such as a HA tag, a FLAG tag, a His tag, a biotin carboxyl carrier protein (BCCP), a c-myc tag, a V5 tag, a glutathione-S-transferase (GST), or a maltose binding protein (MBP) may be used and among them, the His tag is preferably used. The His-tagging protein is specifically trapped on a column of a nickel-nitrilotriacetic acid (Ni-NTA) resin and may be released by EDTA or imidazole.

Yet another exemplary embodiment of the present invention relates to a method of producing psicose from fructose or various elements required for producing the psicose from the fructose. As various elements required for producing the psicose from the fructose, there is a composition for producing the psicose.

An example of the composition for producing the psicose includes a psicose epimerase consisting of the amino acid sequence of SEQ ID NO: 1. Further, another example of the composition for producing the psicose includes a recombinant strain which is transformed by the polynucleotide coding the psicose epimerase consisting of the amino acid sequence of SEQ ID NO: 1 or a recombinant vector including the polynucleotide coding the psicose epimerase consisting of the amino acid sequence of SEQ ID NO: 1, a culture of the recombinant strain, or a lysate of the recombinant strain. In this case, preferably, the composition for producing the psicose may further include one or more kinds selected from the group consisting of manganese ions, nickel ions, and cobalt ions, and more preferably, may further include nickel ions or cobalt ions. The novel psicose epimerase according to the present invention has a metal-loenzyme characteristic in which activation is adjusted by a metal ion and performs the reaction by the enzyme in a presence of a specific metal ion such as nickel ions or cobalt ions to increase a production yield of the psicose.

Further, an example of the method of producing the psicose from the fructose includes reacting the fructose with the psicose epimerase consisting of the amino acid sequence of SEQ ID NO: 1 or the composition including the psicose epimerase. Further, another example of the method of producing the psicose from the fructose includes reacting the fructose with a recombinant strain which is transformed by a polynucleotide coding the psicose epimerase consisting of the amino acid sequence of SEQ ID NO: 1 or a recombinant vector including the polynucleotide coding the psicose epimerase consisting of the amino acid sequence of SEQ ID NO: 1, a culture of the recombinant strain, a lysate of the recombinant strain, or a composition including one or more thereof. Further, the method of producing the psicose from the fructose may additionally include adding metal ions, and a kind of metal ion is as described above. As an example, the metal ion may be added to the fructose that is a substrate or added to a mixture of the enzyme and the fructose. Further, as another example, the metal ion may be added to a carrier immobilized with the enzyme (before adding the fructose), added to a mixture of the carrier immobilized with the enzyme and the fructose (after adding the fructose), or added in a form of the mixture with the fructose when the fructose is added. In the case of using the recombinant strain, the metal ion may be added in the culture or the culturing may be performed in a culture medium added with the metal ion. Further, in the method of producing the psicose from the fructose, the psicose epimerase or the recombinant strain is preferably immobilized in the carrier. The carrier may create an environment in which the activity of the immobilized enzyme may be maintained for a long amount of time, and may be selected from all known carriers which may be used for enzyme immobilization. For example, sodium alginate may be used as the carrier. The sodium alginate is a natural colloidal polysaccharide abundant in the cell wells of algae and consists of β-D-mannuronic acid and α-L-gluronic acid. In terms of the content thereof, the sodium alginate is formed by randomly forming a β-1,4 bond and the strain or the enzyme is stably immobilized, and thus it is advantageous to have excellent psicose yield. As an example, in order to further promote the yield of the psicose, a sodium alginate solution at a concentration of 1.5 to 4.0% (w/v) (for example, an aqueous sodium alginate solution), preferably a sodium alginate solution at a concentration of about 2.5% (w/v) may be used for immobilizing the recombinant strain. Further, in the method of producing the psicose from the fructose, the reaction temperature is in the range of 55 to 67° C., preferably 55 to 65° C., and more preferably 55 to 60° C. when considering stability of the enzyme, and the reaction pH is in the range of 6.5 to 8, preferably 6.5 to 7.5, and more preferably 6.5 to 7. Further, in the method of producing the psicose from the fructose, the concentration of the fructose is not particularly limited thereto, but preferably 35 to 75% (w/w) and more preferably 40 to 70% (w/w) based on the entire reactant when considering productivity and economics. Further, in the method of producing the psicose from the fructose, the amount of used enzyme may be 0.001 to 0.1 mg/ml, preferably 0.01 to 0.1 mg/ml, and more preferably 0.02 to 0.05 mg/ml based on the entire reactant. Further, in the case of producing the psicose from the fructose by using the recombinant strain, the host strain of the recombinant strain is preferably a cytologically safe strain. The cytologically safe strain means a generally accepted as safe (GRAS) strain which is generally accepted as safe and for example, may be a *corynebacterium* strain. The *corynebacterium* strain is an industrial microorganism which produces chemical materials having various uses in fields of feed, medicines, and food, and the like including L-lysine, L-threonine, and various nucleic acids. The *corynebacterium* strain is the GRAS strain and has a strain characteristic which is easily used for gene manipulation and mass culture. Further, the *corynebacterium* strain is a strain having high stability in various process conditions and has a relatively hard cell membrane structure as compared with other bacteria to have a biological characteristic in which the strain is present in a stable state even under high osmotic pressure caused by high sugar concentration. A particular example of the *corynebacterium* strain includes *Corynebacterium glutamicum* and the like.

Example 1: Preparation of Recombinant Strain Producing D-Psicose 3-Epimerase

A genomic DNA was extracted from *Flavonifractor plautii* KCTC 5970 received from Korean Collection for Type Cultures and used as a template, and a polymerase chain reaction (PCR) was performed by using a primer and an Ex-Taq (TAKARA) polymerase for cloning a gene (a polynucleotide of SEQ ID NO: 2) coding D-psicose 3-epimerase.

The following Table 2 lists a primer used for cloning the gene coding the D-psicose 3-epimerase from the genomic DNA of *Flavonifractor plautii*. The primers listed in the following Table 2 were prepared by Bioneer co., KR.

TABLE 2

| SEQ ID NO | Primer type | Base sequence (5'→3') | Restriction enzyme recognition site included in primer |
|---|---|---|---|
| 3 | Forward primer for cloning psicose epimerase | CGG CAT ATG AAC CCG ATT GGA ATG CAC TAC | Nde I |
| 4 | Reverse primer for cloning psicose epimerase | CGG CTC GAG TTA CGC GGT CAG CTC CTT GAG G | Xho I |

Thereafter, only a desired target DNA was isolated from a PCR product by using a gel extraction kit (Qiagen) and then bound to an easy T-vector (Promega). A base sequence analysis of the isolated target DNA was entrusted to Bioneer Co., KR. As a result, it was verified that the target DNA amplified through the PCR corresponded to the polynucleotide of SEQ ID NO: 2. Thereafter, pET-FDPE as a recombinant expression vector was prepared by inserting the target DNA amplified by the PCR reaction to the same restriction recognition site of a pET15b vector (Novagen) as the expression vector by using Nde I and Xho I which were restrictive enzymes. FIG. 1 is a cleavage map of pET-FDPE which is a recombinant expression vector. Thereafter, a recombinant strain was prepared by transforming BL21 (manufacturer: RBC, Taipei, Taiwan) *E. coli* as a competent cell to the pET-FDPE as the recombinant expression vector by using electroporation.

Example 2: Expression and Purification of D-Psicose 3-Epimerase

A single colony of the transformed recombinant strain was inoculated in 15 ml of a LB-ampicillin medium (Difco) and then pre-cultured for about 6 hrs in a condition of 37° C. and 200 rpm. Thereafter, the pre-culture solution was inoculated in 500 ml of a LB-ampicilline medium and shaking-cultured in a condition of 37° C. and 200 rpm. Thereafter, when the absorbance (at 600 nm) of the culture solution was 0.5, IPTG was added to be a concentration of 0.1 mM to induce overexpression of a target enzyme. In this case, the culture from the overexpression inducing time was converted to a condition of 16° C. and 150 rpm and maintained for about 16 hrs. Thereafter, the culture solution of the recombinant strain was centrifuged for 2 mins at 13,000 rpm and a supernatant was removed to collect strain cells of the recombinant strain.

Figure 2:
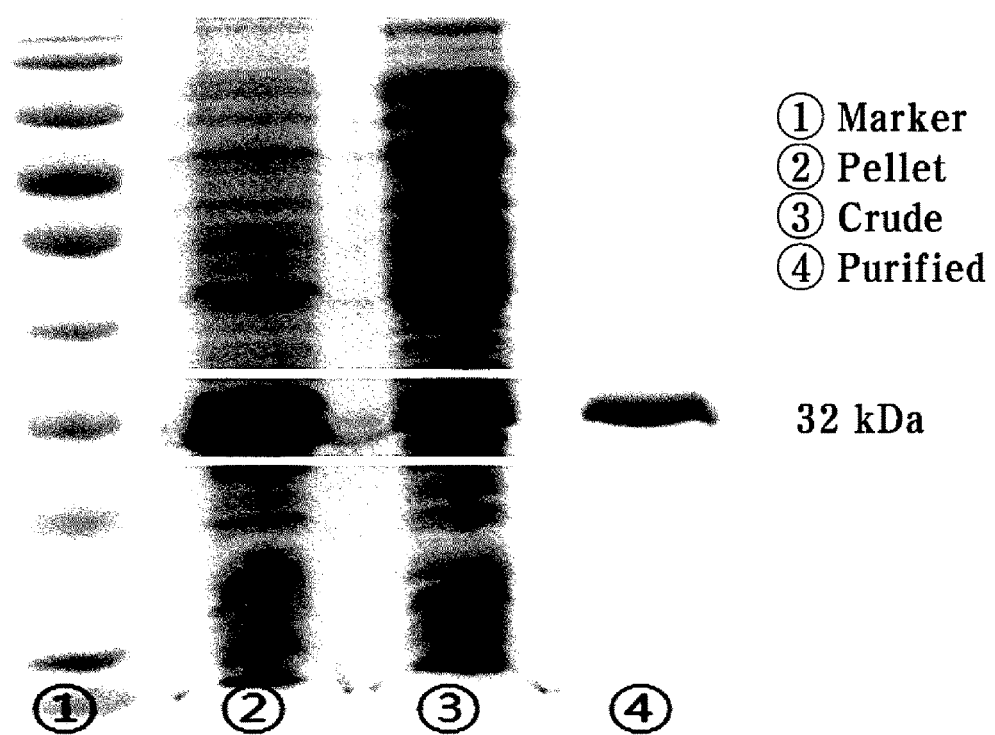
FIG. 2 is a result of performing SDS-PAGE with respect to a D-psicose 3-epimerase purified through a His tag affinity chromatography in Example 2 of the present invention.

The collected strain cells of the recombinant strain were suspended in a lysis buffer (50 mM Tris_HCl 300 mM NaCl pH 8.0, 10 mM imidazole) and then lysed by ultrasonic treatment. The cell lysate was centrifuged for 10 mins at 13,000 rpm and only the supernatant was gathered and then applied to a Ni-NTA column (Bio-Rad, Profinia) pre-equilibrated with a lysis buffer, and buffer solutions including 20 mM imidazole and 200 mM imidazole were sequentially flowed in 50 mM Tris_HCl 300 mM NaCl pH 8.0. Finally, 50 mM Tris_HCl 300 mM NaCl pH 8.0 and 200 mM imidazole were flowed to elute a target protein. It was verified from an experimental result to be described below that eluted protein was the D-psicose 3-epimerase. Thereafter, the eluted protein was stored in a buffer solution (PIPES, pH 7.5) for measuring an enzyme activity so as to be used for a next experiment. Further, the SDS-PAGE for the eluted protein was performed, and thus, it was verified that the size of the eluted protein was 32 kDa. FIG. 2 is a result of performing SDS-PAGE for a D-psicose 3-epimerase purified through a His tag affinity chromatography in Example 2 of the present invention.

Figure 3:
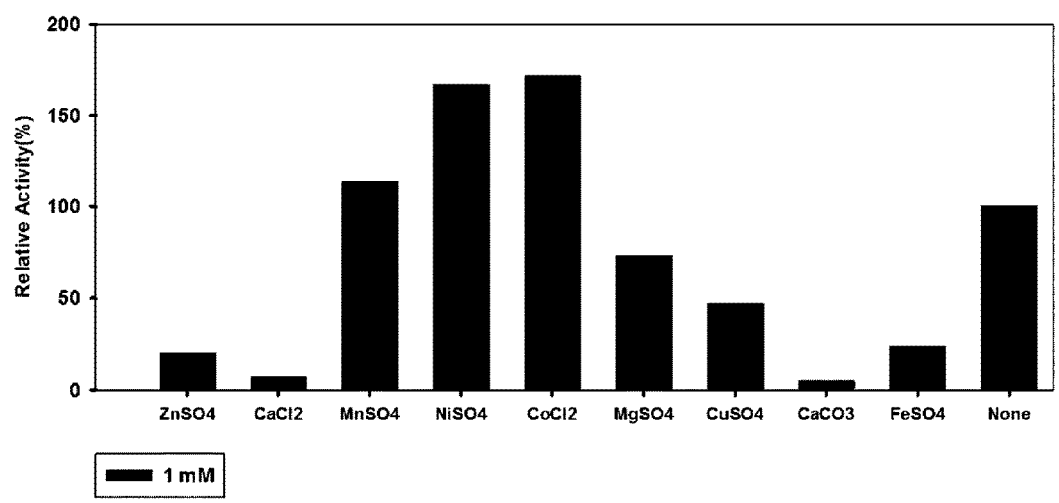
FIG. 3 is a graph illustrating an activity of the D-psicose 3-epimerase of the present invention according to a kind of added metal ion.

Example 3: Verification of Characteristics of D-Psicose 3-Epimerase (1) Analysis of Metal Ion Requirement of D-Psicose 3-Epimerase Whether the metal ion had an effect on the D-psicose 3-epimerase obtained in Example 2 was examined. $ZnSO_4$, $CaCl_2$, $MnSO_4$, $NiSO_4$, $CoCl2$, $MgSO_4$, $CuSO_4$, $CaCO_3$, and $FeSO_4$ were put in the purified enzyme buffer solution (PIPES, pH 7.5) to be 1 mM, respectively and then the metal ions were bound to the enzymes for about 1 hr. Thereafter, the enzymes bound with the metal ions were mixed with a 100 mM aqueous fructose solution as a substrate at a weight ratio of 1:1 and the mixture in which the enzyme concentration was 0.025 ml/mg and the fructose concentration was 50 mM was made and reacted for 10 mins at 60° C. Then, a hydrochloric acid solution was added thereto to stop the reaction. Further, in a control group, the same experiment was performed by using an enzyme (None) without treating the metal ion. Thereafter, an amount (mM) of produced psicose was measured and divided into an enzyme amount and a reaction time to calculate an enzyme activity. The psicose amount was analyzed by HPLC. The HPLC analysis was performed while water 100% (v/v) as a mobile phase flowed at a flow velocity of 0.6 ml/min at 80° C. by using a 87C (BIO-RAD) column and the psicose was detected with a refractive index detector (Agilent 1260 TID) to analyze the produced amount of psicose. FIG. 3 is a graph illustrating an activity of the D-psicose 3-epimerase of the present invention according to a kind of added metal ion. In FIG. 3, an enzyme activity in the case of treating each metal ion is relatively represented by setting an enzyme activity in a control group to 100. As illustrated in FIG. 3, in the D-psicose 3-epimerase obtained in Example 2, an activity of converting the fructose into the psicose was increased by adding manganese ions, nickel ions, and cobalt ions, and particularly, an increase in activity of the nickel ions and cobalt ions was significant.

Figure 4:
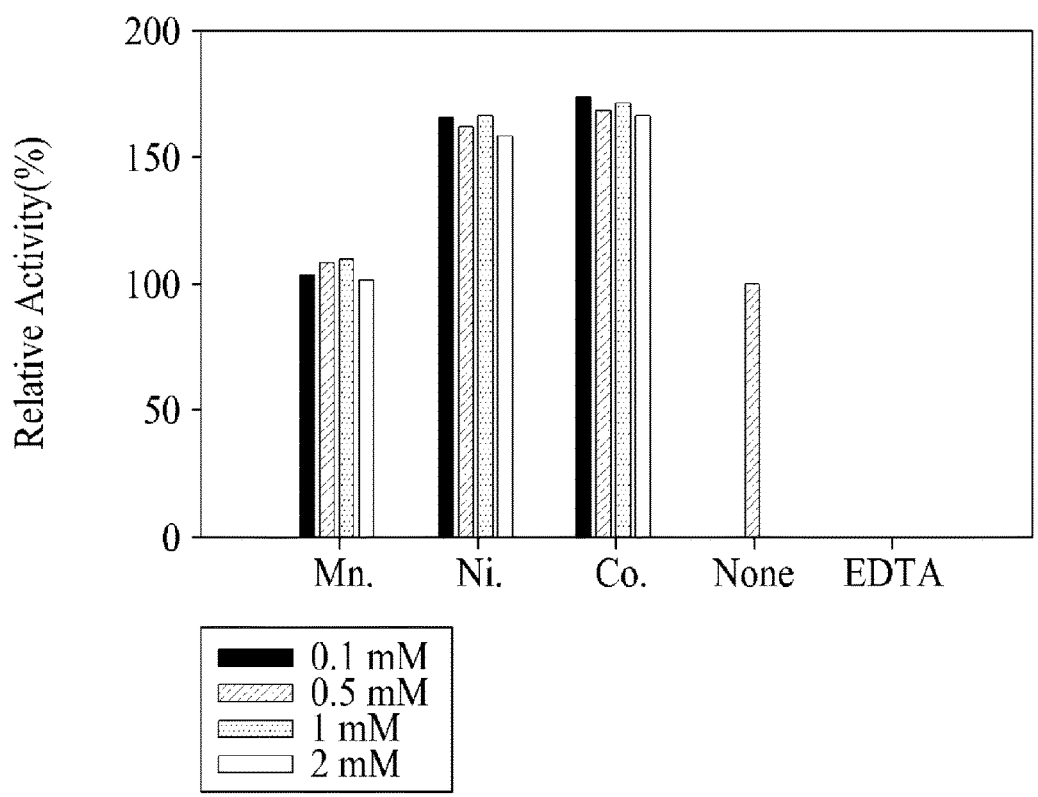
FIG. 4 is a graph illustrating an activity of the D-psicose 3-epimerase of the present invention for each kind of added metal ion and each treated concentration.

Thereafter, $MnSO_4$, $NiSO_4$, and $CoCl_2$ were treated at various concentrations in the purified D-psicose 3-epimerase solution and then the same experiments were performed. FIG. 4 is a graph illustrating an activity of the D-psicose 3-epimerase of the present invention for each kind of added metal ion and each treated concentration. As illustrated in FIG. 4, the manganese ions, the nickel ions, and the cobalt ions increased the activity of the D-psicose 3-epimerase in various concentration ranges.

Figure 5:
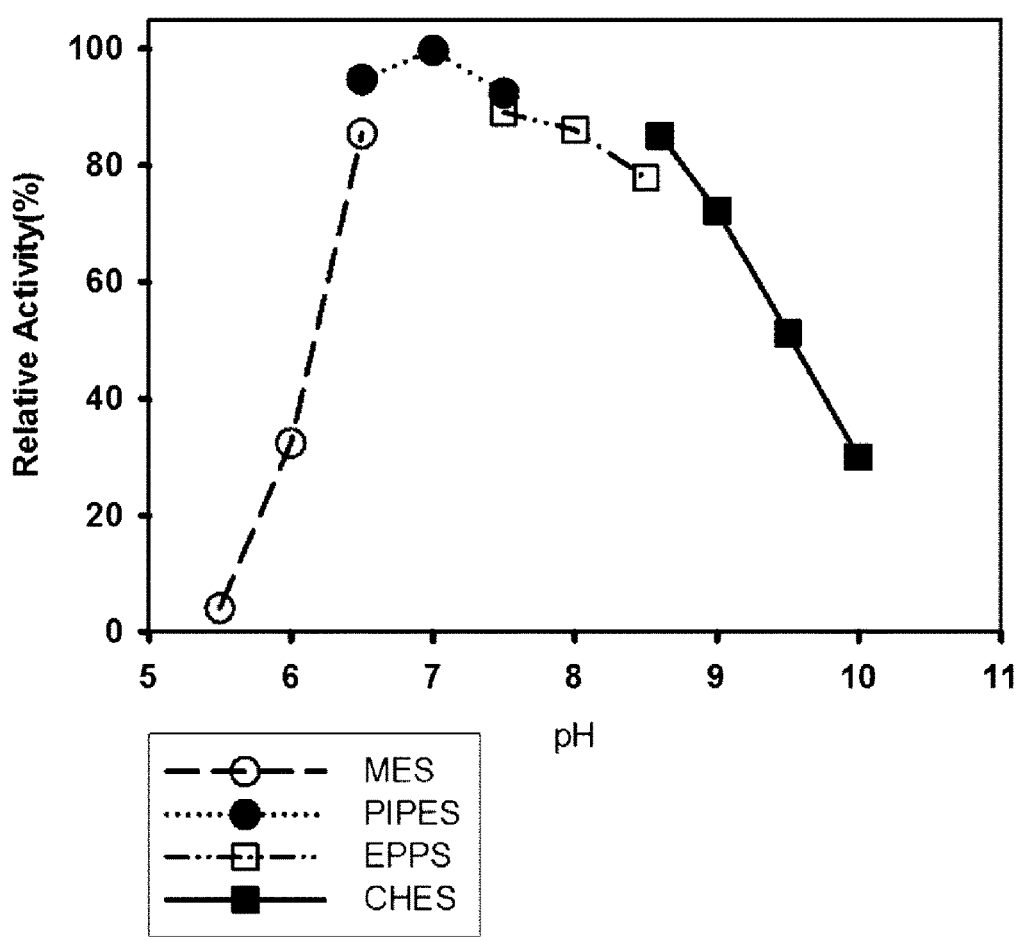
FIG. 5 is a graph illustrating an activity of the D-psicose 3-epimerase of the present invention for each reaction pH.

(2) Analysis of Activity of D-Psicose 3-Epimerase According to Change in pH or Temperature In order to examine an optimal pH of the D-psicose 3-epimerase obtained in Example 2, test solutions of various pHs were made by using an MES buffer, a PIPES buffer, an EPPS buffer, and a CHES buffer. In detail, $NiSO_4$ was treated at a concentration of 1 mM in a buffer solution of the purified enzyme and then mixed with a 100 mM aqueous fructose solution at a weight ratio of 1:1 to prepare the test solutions of various pHs having the buffer concentration of 50 mM, the enzyme concentration of 0.025 ml/mg, and the fructose concentration of 50 mM. Thereafter, the test solutions reacted for 10 mins at 60° C. and a hydrochloric acid solution was added thereto to stop the reaction. Thereafter, the amount (mM) of produced psicose was analyzed and measured by the HPLC and divided into an enzyme amount and a reaction time to calculate an enzyme activity. FIG. 5 is a graph illustrating an activity of the D-psicose 3-epimerase of the present invention for each reaction pH. In FIG. 5, the enzyme activity is relatively represented by setting a maximum activity to 100. As illustrated in FIG. 5, the D-psicose 3-epimerase of the present invention had a high activity at pH of 6.5 to 8 and preferably pH of 6.5 to 7.5 and had a maximal activity at pH 7.

Figure 6:
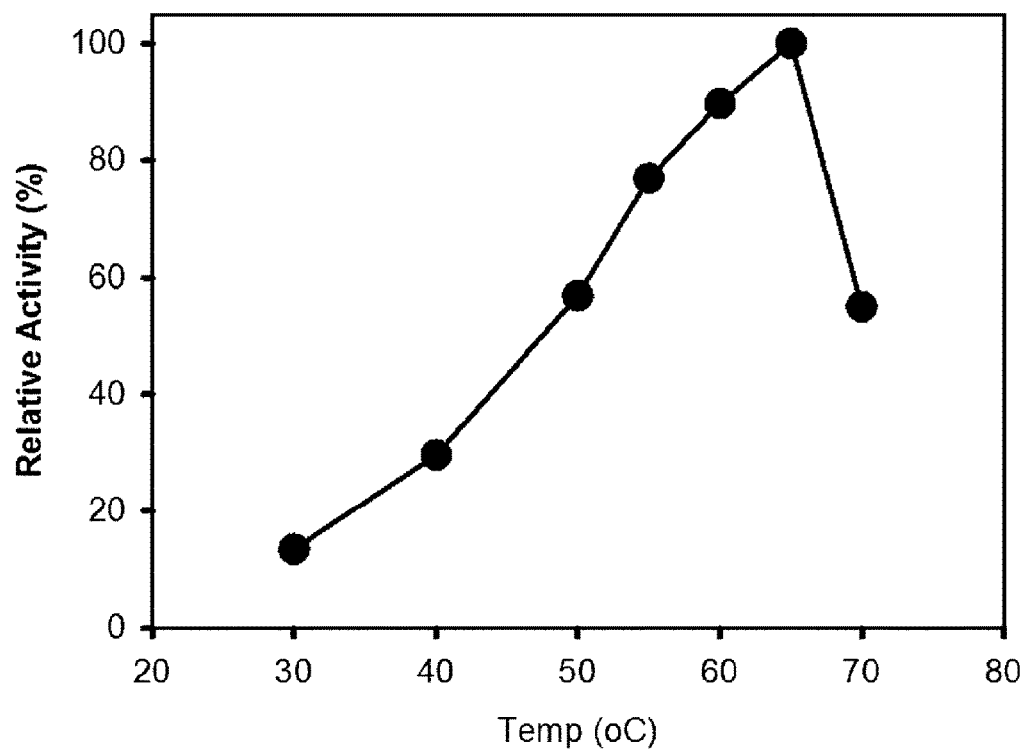
FIG. 6 is a graph illustrating an activity of the D-psicose 3-epimerase of the present invention for each reaction temperature.

Further, $NiSO_4$ was treated at a concentration of 1 mM in a buffer solution (PIPES, pH 7.5) of the purified enzyme and then mixed with a 100 mM aqueous fructose solution at a weight ratio of 1:1 to prepare a test solution having pH 7.0, the enzyme concentration of 0.025 ml/mg, and the fructose concentration of 50 mM. Thereafter, the test solution reacted for 10 mins at various temperatures and then a hydrochloric acid solution was added thereto to stop the reaction. Thereafter, the amount (mM) of produced psicose was analyzed and measured by the HPLC and divided into an enzyme amount and a reaction time to calculate an enzyme activity. FIG. 6 is a graph illustrating an activity of the D-psicose 3-epimerase of the present invention for each reaction temperature. In FIG. 6, the enzyme activity is relatively represented by setting a maximum activity to 100. As illustrated in FIG. 6, the D-psicose 3-epimerase of the present invention had a high activity at a temperature of 55 to 67° C. and had a maximal activity at 65° C.

(3) Analysis of Substrate Specificity of D-Psicose 3-Epimerase

Reaction activities for various substrates such as psicose, fructose, and tagatose of the D-psicose 3-epimerase obtained in Example 2 were analyzed.

Figure 7:
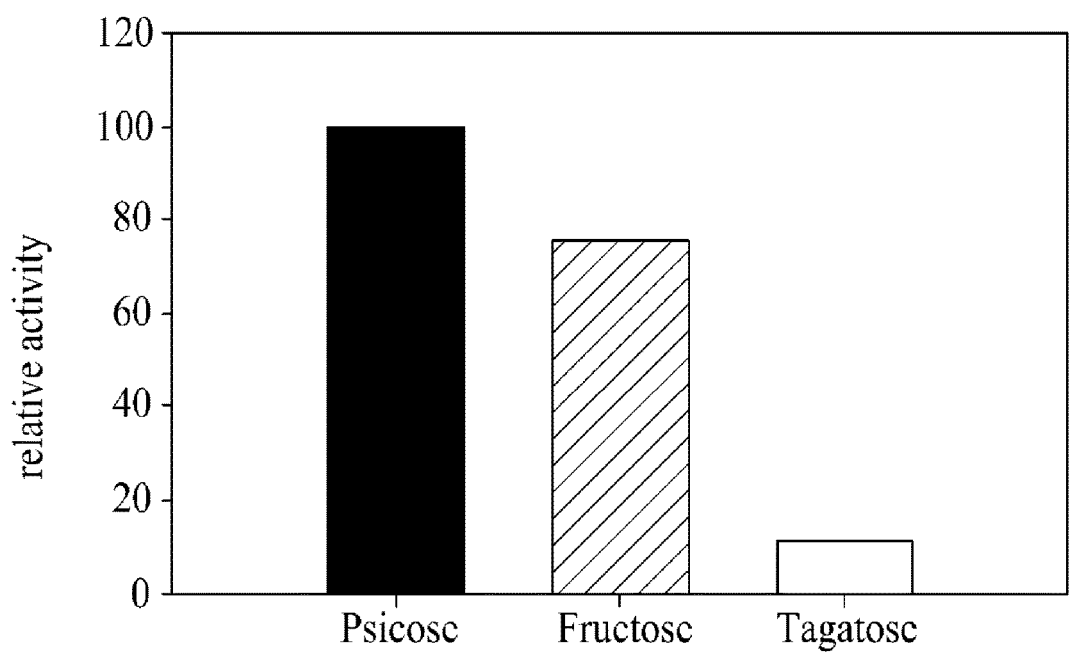
FIG. 7 is a graph illustrating an activity of the D-psicose 3-epimerase of the present invention for each substrate.

$NiSO_4$ was treated at a concentration of 1 mM in a buffer solution (PIPES, pH 7.5) of the purified enzyme and then mixed with a 100 mM aqueous substrate solution at a weight ratio of 1:1 to prepare a test solution having pH 7.0, the enzyme concentration of 0.025 ml/mg, and the substrate concentration of 50 mM. Thereafter, the test solution reacted for 10 mins at 65° C. and then a hydrochloric acid solution was added thereto to stop the reaction. Thereafter, an amount (mM) of epimer corresponding to the substrate was analyzed and measured by the HPLC and divided into an enzyme amount and a reaction time to calculate an enzyme activity. FIG. 7 is a graph illustrating an activity of the D-psicose 3-epimerase of the present invention for each substrate. In FIG. 7, the enzyme activity is relatively represented by setting an enzyme activity of a reaction of using psicose as a substrate to 100. As illustrated in FIG. 7, it was determined that the D-psicose 3-epimerase of the present invention had a high activity for psicose and fructose, and particularly, the activity of converting the fructose into the D-psicose was very high as compared with the existing D-psicose 3-epimerase. Therefore, the D-psicose can be produced from the fructose in a high yield by using the D-psicose 3-epimerase of the present invention.

(4) Analysis of Thermal Stability of D-Psicose 3-Epimerase

The D-psicose 3-epimerase obtained in Example 2 was prepared in a 50 mM PIPES buffer solution to be a concentration of 0.05 mg/ml and then, the obtained solutions were put and stored in water bathes set at temperatures of 55° C., 60° C., 65° C., and 70° C., respectively, to heat. A buffer solution of the purified enzyme was ejected for each stored time and treated with $NiSO_4$ at a concentration of 1 mM, and then mixed with a 100 mM aqueous substrate solution at a weight ratio of 1:1 to prepare a test solution having pH 7.0, the enzyme concentration of 0.025 ml/mg, and the substrate concentration of 50 mM. Thereafter, the test solution reacted for 10 mins at 65° C. and then a hydrochloric acid solution was added thereto to stop the reaction. Thereafter, the amount (mM) of produced psicose was analyzed and measured by the HPLC and divided into an enzyme amount and a reaction time to calculate an enzyme activity. As a result, even though the buffer solution of the purified enzyme was heated for 250 mins at 55° C., the enzyme activity was maintained as it is. Further, when the buffer solution of the purified enzyme was heated for about 200 mins at 60° C., the enzyme activity was reduced by about 80% as compared with before heat treatment. Generally, when it is considered that most of D-psicose 3-epimerase has a half-life (a heat treatment time when the enzyme activity is 50% as compared with before heat treatment) of approximately one hour at 50° C., the D-psicose 3-epimerase of the present invention has very excellent thermal stability.

(5) Analysis of Activity of D-Psicose 3-Epimerase in High Concentration of Fructose 700 μl of fructose at a concentration of 70 wt % was preheated at 60° C. and added with 280 μl of a PIPES buffer solution at 0.1 mg/ml of a concentration of the D-psicose 3-epimerase obtained in Example 2 and then, the obtained reactant was reacted at 60° C. The reaction product was taken by 10 μl for each reaction time and diluted 25 times. A hydrochloric acid solution was added to the diluted product to stop the reaction. Thereafter, the amount (mM) of produced psicose was analyzed and measured by the HPLC and divided into an amount of the fructose used as the substrate to calculate a conversion rate. A conversion rate of fructose into psicose for each reaction time is listed in the following Table 3. As listed in Table 3, when the D-psicose 3-epimerase of the present invention reacted with the high-concentrated fructose, the conversion rate reached a maximum conversion rate exceeding 33% only for about 18 hrs.

TABLE 3

| Reaction elapse time (hr) | Conversion rate (%) of fructose into psicose |
| --- | --- |
| 1 | 9.04 |
| 2 | 15.20 |
| 3 | 19.52 |
| 4 | 22.36 |
| 5 | 24.66 |
| 6 | 26.75 |
| 7 | 27.94 |
| 18 | 33.62 |
| 28 | 33.67 |

As described above, the present invention has been described through the Examples, but is not always limited thereto, and various modified embodiments can be made within the range not departing from the scope and spirit of the present invention. Therefore, it should be interpreted that the scope of the present invention includes all embodiments belonging to claims accompanied in the present invention.

What is claimed is:

1. A method for producing psicose, the method comprising:

reacting fructose with a psicose epimerase consisting of the amino acid sequence of SEQ ID NO: 1.

2. The method for producing psicose of claim 1, wherein the psicose epimerase is obtained from *Flavonifractor plautii*.

3. The method for producing psicose of claim 1, wherein the composition further includes one or more kinds selected from the group consisting of manganese ions, nickel ions, and cobalt ions.

4. The method for producing psicose of claim 1, wherein a temperature of the reaction is 55 to 67° C. and a pH of the reaction is 6.5 to 8.

5. The method for producing psicose of claim 1, wherein the concentration of the fructose is 35 to 75% (w/w).

6. The method for producing psicose of claim 1, wherein the psicose epimerase is immobilized in a carrier.

* * * * *

SEQUENCE LISTING

```
<160> NUMBER OF SEQ ID NOS: 4

<210> SEQ ID NO 1
<211> LENGTH: 294
<212> TYPE: PRT
<213> ORGANISM: Artificial Sequence
<220> FEATURE:
<223> OTHER INFORMATION: D-psicose 3-epimerase derived from
      Flavonifractor plautii

<400> SEQUENCE: 1

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110
```

Gly Trp Gln Ala Leu Pro Asp His Gly Ile Thr Leu Asp Glu Lys Arg
            115                 120                 125

Arg Lys Glu Glu Leu Ala Leu Glu Ser Met Ser Arg Leu Met Lys Val
130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Gly Glu Asn Asn Arg Arg Pro Ala Gly
    210                 215                 220

Ser Thr Asn Arg Leu Pro Trp Lys Asp Met Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

```
<210> SEQ ID NO 2
<211> LENGTH: 885
<212> TYPE: DNA
<213> ORGANISM: Artificial Sequence
<220> FEATURE:
<223> OTHER INFORMATION: polynucleotide coding D-psicose 3-epimerase
      derived from Flavonifractor plautii

<400> SEQUENCE: 2
atgaacccga ttggaatgca ctacggcttc tggagccaca actgggacga gattgcatac      60 ataccctga tggagaagct ggcctggctg gctttgaca tctgcgaggt ggcctccgcc      120
gagtggggct attacgacga cgccaggctg cgggagctga aggcctgcgc cgatcacaac      180
ggcctgggca tcacctattc catcggcctg gaggccaaat acgacctggc cagcgacgat      240
ccggcggtgc gggagaacgg catccgccat gtcacccgca tcctggagag catgcccaag      300 gtggggcgg ccatcctcaa cggcgtgtcc tacgccgggt ggcaggccct gcccgaccac      360
ggaatcaccc tggacgagaa gcgccgcaag gaggagcttg ccctggagtc catgtcccgg      420
ctcatgaagg tggcggagga ctgcggcgtg ctctactgct gcgaggtggt caaccgcttc      480
gagcagtacc tgctcaacac cgccaaagag ggcgtggagt ttgtcaagcg cctgggcagt      540
cccaacgccc gggtgctgct ggataccttc cacatgaaca tcgaggagga cagcatggtg      600
gacgccattc tggaggcggg ccctggctg gggcatttcc acgtggggga gaacaaccgc      660
cgccccgccg gctccaccaa ccgcctgccc tggaaggaca tggccgccgc cctcaagcag      720
gtgaactacc agggggccat tgtgatggag cccttcgtgc tcatggggggg taccattccc      780 tatgatatca aggtctggcg ggatctcagc ggcgggggccg gggaggccgg gctggacgag      840
atggcgggcc gggcctgccg gttcctcaag gagctgaccg cgtaa      885

<210> SEQ ID NO 3
```

-continued

```
<211> LENGTH: 30
<212> TYPE: DNA
<213> ORGANISM: Artificial Sequence
<220> FEATURE:
<223> OTHER INFORMATION: forward primer for cloning D-psicose 3-
      epimerase

<400> SEQUENCE: 3
cggcatatga acccgattgg aatgcactac                                         30

<210> SEQ ID NO 4
<211> LENGTH: 31
<212> TYPE: DNA
<213> ORGANISM: Artificial Sequence
<220> FEATURE:
<223> OTHER INFORMATION: reverse primer for cloning D-psicose 3-
      epimerase

<400> SEQUENCE: 4
cggctcgagt tacgcggtca gctccttgag g                                       31
```